United States Patent [19]
Porrata

[11] Patent Number: 6,146,347
[45] Date of Patent: Nov. 14, 2000

[54] APPLIANCE AND METHOD FOR TREATING CARPAL TUNNEL SYNDROME

[76] Inventor: Humberto L. Porrata, 144 W. 23 St., #3E, New York, N.Y. 10011

[21] Appl. No.: 09/088,265

[22] Filed: Jun. 1, 1998

[51] Int. Cl.[7] .................................. A61F 5/00; A61F 5/37
[52] U.S. Cl. .................................. 602/21; 602/6; 602/13; 128/879
[58] Field of Search .................................. 602/8, 12, 13, 602/20–22, 60–64, 5, 23, 26, 27; 128/878, 879, DIG. 20

[56] References Cited

U.S. PATENT DOCUMENTS

| | | | |
|---|---|---|---|
| 2,388,330 | 11/1945 | Jungmann | 2/16 |
| 2,823,668 | 2/1958 | Van Court et al. | 602/13 |
| 4,067,063 | 1/1978 | Ettinger | 2/413 |
| 4,378,009 | 3/1983 | Rowley et al. | 602/13 |
| 4,787,376 | 11/1988 | Eisenberg | 2/20 |
| 5,014,689 | 5/1991 | Meunchen et al. | |
| 5,256,136 | 10/1993 | Sucher | |
| 5,385,537 | 1/1995 | Davini | |
| 5,417,645 | 5/1995 | Lemmen | |
| 5,441,058 | 8/1995 | Fareed | 128/878 X |
| 5,468,220 | 11/1995 | Sucher | |
| 5,613,941 | 3/1997 | Prengler | 602/13 |
| 5,647,850 | 7/1997 | Allen | 604/116 |
| 5,702,355 | 12/1997 | Repice et al. | |

Primary Examiner—Stephen R. Crow
Assistant Examiner—Denise Pothier
Attorney, Agent, or Firm—Schweitzer Cornman Gross & Bondell LLP

[57] ABSTRACT

A method and appliance for treating carpal tunnel syndrome has a splint with dorsal, thenar and hypothenar portions for applying pressure to the respective dorsal aspect of the hand and to thenar and hypothenar areas of a palmar aspect of the hand to induce stretching of the carpal ligament and flexor retinaculum. The thenar and hypothenar portions of the splint are connected to opposite sides of the dorsal portion and are spaced from the dorsal portion to allow for the insertion of the hand to be treated. The splint is preferably formed from a unitary piece of substantially rigid material and is sized and shaped to closely receive the hand with the dorsal, thenar and hypothenar portions substantially aligned with and covering the respective dorsal aspect, and thenar and hypothenar areas of the palmar aspect of the hand. An inflatable bladder, connected to a controllable fluid source, is located to contact, the dorsal aspect of the hand between the thenar and hypothenar areas of the palmar aspect to induce stretching of the carpal ligament and flexor retinaculum. A pressure gauge is connected to the bladder for monitoring. The controllable source of pressurized fluid is adjustable during treatment. The thenar portion of the splint can be releasably attachable with securing means to aid in insertion of the hand into the splint. In the method of use, the hand is inserted into the splint and the bladder is pressurized to apply pressure and induce stretching. The pressure is maintained at a constant or varying level for a predetermined period of time.

11 Claims, 9 Drawing Sheets

APPLIANCE AND METHOD FOR TREATING CARPAL TUNNEL SYNDROME

FIELD OF THE INVENTION

This invention pertains to the field of methods and appliances for the treatment of carpal tunnel syndrome.

BACKGROUND AND SUMMARY OF THE INVENTION

Carpal tunnel syndrome is caused by a deleterious increase in pressure on the median nerve which passes through the carpal tunnel (or canal) in the hand, adjacent the wrist. The deleterious increase in pressure, which is brought on by prolonged repetitive motion of the hand and digits, is often caused by inflammation or damage to tendons for the hand which pass through the carpal tunnel along with the median nerve. Pressure increases can also be caused by narrowing of the carpal canal and by generalized swelling of the structures in the hand.

The carpal tunnel is formed by the eight carpal bones of the hand adjacent the wrist, which bones are arranged in two rows forming a generally U-shaped inverted arch-like "tunnel" structure. The three large carpal bones of the proximal row (i.e., closest to the chest), beginning laterally (i.e., from the outside with the hand directed downward and the palm facing forward), are the scaphoid, lunate, and triquetrum; the smaller pisiform bone sits on the palmar surface of the triquetrum. The distal row, from lateral to medial, consists of the trapezium, trapezoid, capitate, and hamate carpal bones.

The vault of the carpal tunnel is formed by the carpal ligament and the flexor retinaculum. Nine tendons, their tendon sheaths, and the median nerve pass through the tunnel.

The carpal ligament is made of collagen and elastin and extends from the pisiformis and hamulus of hamate bones on the ulnar aspect of the tunnel to the tubercle (i.e., projection) of trapezium and the tubercle of the scaphoid bones on the radial (i.e. lateral) aspect of the carpal tunnel. The flexor retinaculum also stretches across the carpal tunnel and attaches to, on the medial aspect of the carpal tunnel, the pisiform bone and the hook of hamate, and, on the lateral aspect, the tubercle of the scaphoid and trapezium bones. The proximal border of the flexor retinaculum corresponds generally to the transverse skin crease at the base of the hand/wrist. The carpal ligament and flexor retinaculum, along with the carpal bones, form the restricted space through which the median nerve and several tendons pass.

Symptoms of carpal tunnel syndrome include tingling sensation in the hand, discomfort, numbness, and pain localized in the hand or radiating up the arm to the shoulder. All of these symptoms can occur during the day or can make the patients wake up at night. In advanced cases, there is atrophy and weakness of the thenar area of the hand which may weaken the grip and cause objects to fall out of the hand.

Conventional treatment of carpal tunnel syndrome is divided into surgical and conservative (non-invasive). Surgical treatment consists of making an incision on the palmar aspect of the hand and splitting the carpal ligament, thus partially opening the carpal tunnel and relieving the pressure. This procedure, while often successful, may have negative consequences, which include, but are not limited to, non-resolution of symptoms often requiring a second surgery, pain in the area of the scar, and injury to the superficial palmar branch of the median nerve causing persistent neurologic symptoms. Understandably, surgical treatment is often considered as a last option.

Conservative, non-invasive treatment includes immobilizing the hand and wrist, usually with a resting splint to maintain the hand in a neutral position (such as disclosed in U.S. Pat. No. 5,014,689), mechanical stretching of the carpal ligament (such as disclosed in U.S. Pat. No. 5,468,220), care provider administered massage, anti-inflammatory medications, cortisone injections, and avoidance of the daily activities which cause the symptoms, including a change in job. However, none of the known methods and devices provide for precise and controllable stretching of both the carpal ligament and the flexor retinaculum in a comfortable manner.

The objective of the present invention is to stretch the carpal ligament and the flexor retinaculum, as well as the superficial structures of the hand, in a safe manner under precise patient control. The new method and new appliance of prevention are inexpensive, prevent progression of carpal tunnel syndrome and provide relief from symptoms by increasing the cross sectional area of the carpal tunnel, thus decreasing compression on the median nerve and decreasing the resulting symptoms.

Controlled and monitored use of the appliance of the invention dynamically treats carpal tunnel syndrome through the application of pressure to large portions of the palm of the hand (in the thenar and hypothenar areas) while at the same time providing application of pressure, in the opposite direction, to a large portion of the dorsum of the hand with an air bladder. This novel procedure stretches the carpal ligament, the flexor retinaculum, and superficial structures of the hand in the palmar aspect of the hand, in a readily, safely controllable and comfortable manner.

Considering that the constitutions of the carpal ligament and the flexor retinaculum are soft tissue composed of collagen and elastin, stretching the carpal ligament and the flexor retinaculum is effective for decreasing compression on the median nerve by increasing the diameter of the tunnel and decreasing the rigidity of the retinaculum and the carpal ligament, thus alleviating the symptoms of carpal tunnel syndrome.

BRIEF DESCRIPTION OF THE DRAWINGS

For a more complete understanding of the invention and other of its features and advantages, reference should be made to the following detailed description of the preferred embodiments of the invention in conjunction with the accompanying drawings, wherein.

DETAILED DESCRIPTION OF THE INVENTION

Figure 1:
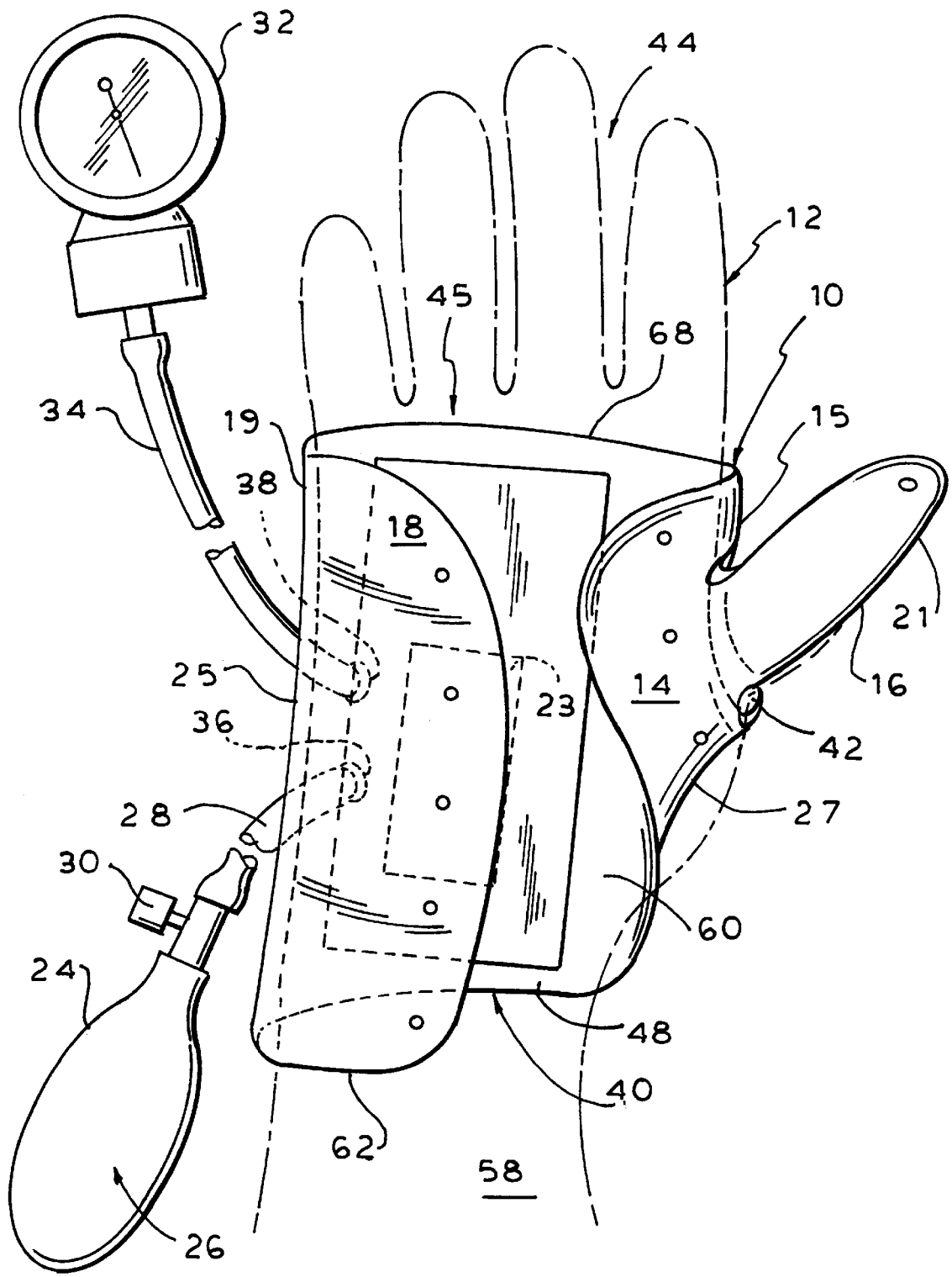
FIG. 1 is a top plan view of a first embodiment of the new therapeutic appliance of the invention.
Figure 2:
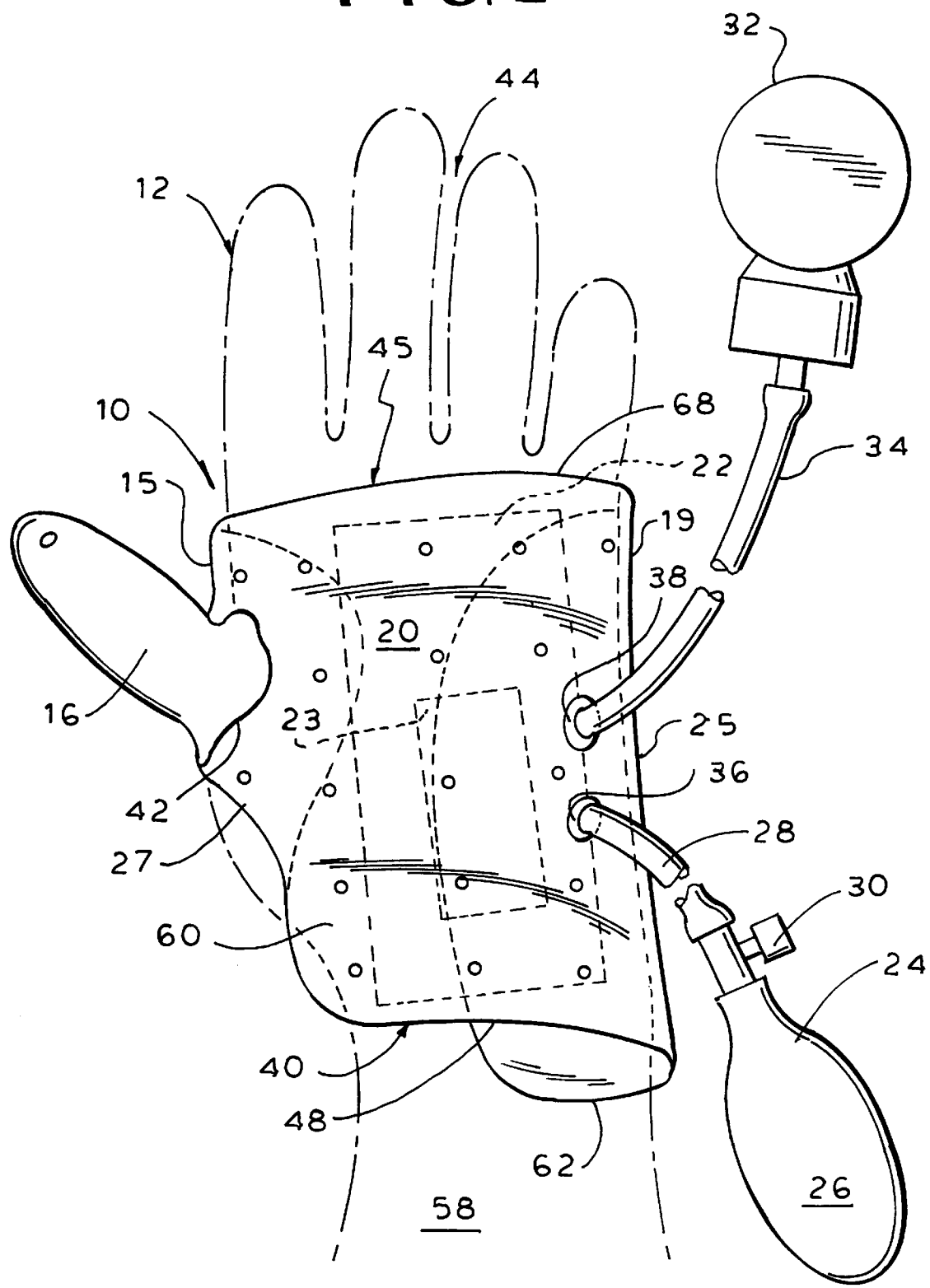
FIG. 2 is a bottom plan view of the appliance of FIG. 1.
Figure 3:
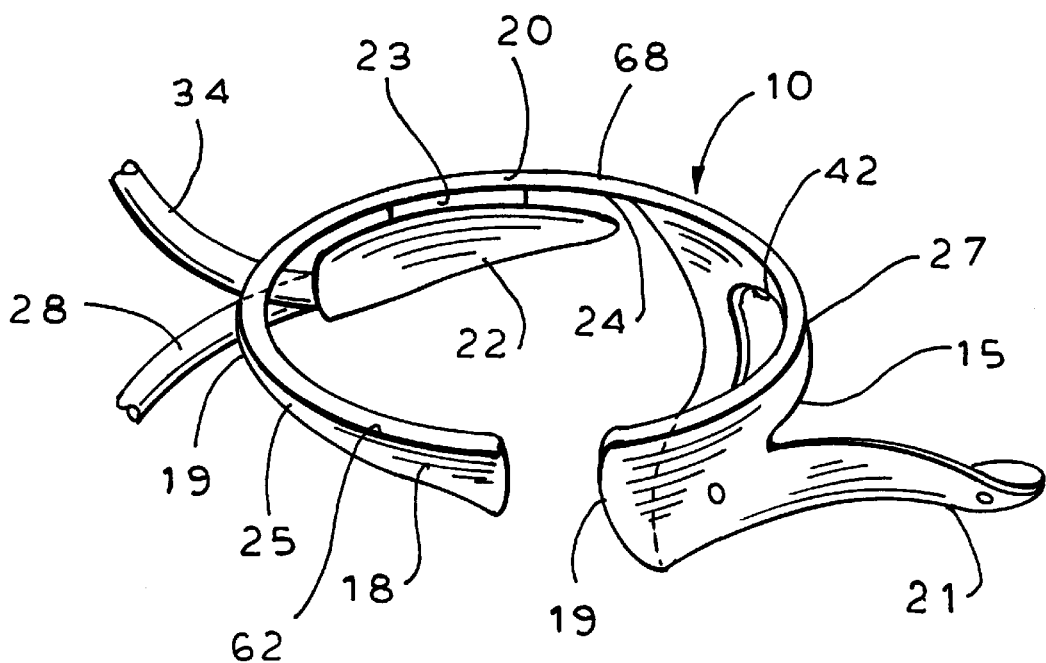
FIG. 3 is a distal end elevational view of the appliance of FIG. 1.

Referring to the drawings, and initially to FIGS. 1–3 thereof, a first embodiment of the therapeutic appliance 10 of the invention is applied to the hand 12 of a person. The appliance 10 includes a thenar portion 14 which applies pressure to a substantial portion of the thenar area of the palmar aspect of the hand 12 and a hypothenar portion 18 which applies pressure to a substantial portion of the hypothenar area of the palmar aspect of the hand 12. Opposite, and spaced from the thenar and hypothenar portions 14, 18 is a dorsal portion 20 which is adapted to support the dorsal aspect of the hand. The splint 10, including the thenar, hypothenar and dorsal portions 14, 18, 20, is sized and shaped to conform to the shape of the associated areas of the hand such that the hand is closely received within the splint.

The thenar and hypothenar portions 14, 18 are each located between opposite sides of the dorsal portion and are connected to the dorsal portion by lateral and medial joining portions 15, 19 respectively. The lateral joining portion 15 includes a hole 42 for the thumb 16 and is adapted to maintain the thumb in radial abduction.

A thumb support extension 21 preferably extends outwardly from the thenar portion 14 to prevent the thumb 16 from flexing during treatment. The thumb support extension 21 can be integrally connected to the thenar portion 14, formed from the material removed from the lateral joining portion 15 when forming the thumb hole 42.

An inflatable bladder 22 is attached to an interior surface 24 of the dorsal portion 20 of the appliance 10, preferably with a fastener 23, such as a Velcro® hook-and-loop fastener, or the like. The bladder 22 is located between opposite sides 25, 27 of the appliance 10 to apply pressure generally to the center of the dorsal aspect of the hand 12 between the thenar and hypothenar areas of the palmar aspect of the hand, and is sized to apply pressure to a substantial portion of the dorsal aspect of the hand.

A controllable source of pressurized fluid 24, such as the hand-operated bulb pump 26 shown, or the like, is connected to the bladder 22 via a first conduit 28, which is preferably made of flexible rubber tubing. The source of pressurized fluid 24 preferably includes a release valve 30 to decrease the pressure in the bladder 22 when desirable. A pressure gauge 32 or sphygmomanometer is also preferably connected to the bladder 22 via a second conduit 34 to monitor the pressure in the bladder 22 in, for example mm Hg. The appliance 10 includes orifices 36, 38 (best seen in FIG. 2) through which the first and second conduits 28, 34 pass. The appliance 10 may also include an adjustable, automatic pressure release valve (not shown) or other suitable means to set a maximum allowable pressure for the bladder 22.

To don the appliance 10, the hand 12 is inserted through a first end 40 of the appliance 10, between the bladder 22 and the thenar and hypothenar portions 14, 18, with the bladder 22 in a deflated condition. The thumb 14 is inserted through a thumb hole 42 formed between the thenar and dorsal portions 14, 20, with the fingers 44 projecting past a second end 45 of the appliance 10. When the hand 12 is inserted, the thumb 16 is maintained in radial abduction, as shown.

The thenar, hypothenar, and dorsal portions 14, 18, and 20 of the appliance 10 are preferably integrally formed from relatively rigid material sized and shaped to envelop the hand 12. Suitable material is preferably between 1/16" and 1/4" thick Rolyan® Aquaplast® splinting material available from Smith and Nephew, Inc. in Germantown, Wis., or the like. The appliance 10 is adapted to be manufactured in general "small-medium-large" sizes, each for a limited range of hand shapes and sizes. However, the appliance 10 is preferably individually sized for each user by using the patient's hand as a model or mold. In addition, the appliance may include ventilation holes to allow forced or convective cooling air to pass over the hand during treatment.

The dorsal portion 20 of the appliance 10 is preferably straight in a longitudinal direction and includes a proximal end portion 48 which extends toward the forearm 58, beyond the proximal end 60 of the hand 12 to prevent the hand 12 from extending upward during treatment.

The hypothenar portion 18 of the appliance is also preferably straight in a longitudinal direction, and includes a proximal end portion 62 which extends toward the forearm 58, beyond the proximal end 60 of the hand 12 to prevent the hand 12 from flexing during treatment. Thus, the hand 12 is substantially maintained in the neutral position during treatment and is substantially prevented from flexing or extending. Alternatively, a wrist strap (not shown) may be connected to the dorsal portion 20 of the appliance 10, around the forearm 58 to maintain the hand 12 in the neutral position.

Figure 8:
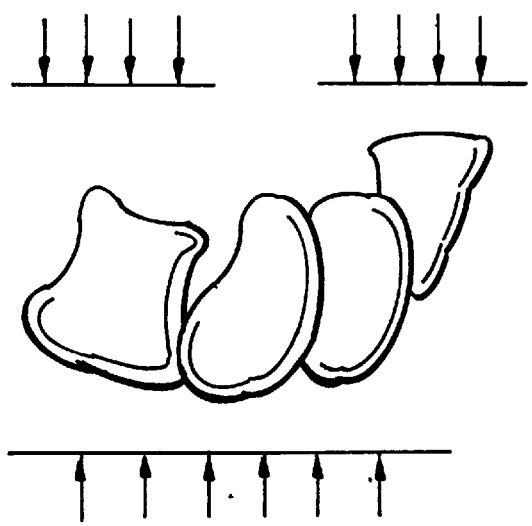
FIG. 8 is a proximal end elevational schematic view of the carpal bones of the hand subject to forces applied by the appliance of FIG. 4.
Figure 9:
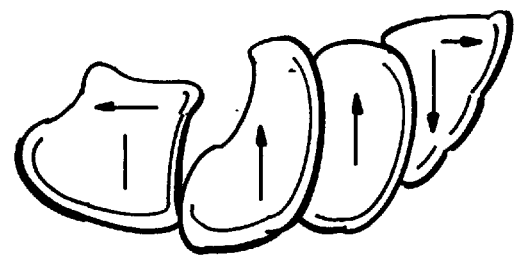
FIG. 9 is a proximal end elevational schematic view of the carpal bones of the hand as displaced by the forces indicated in FIG. 8.
Figure 10:
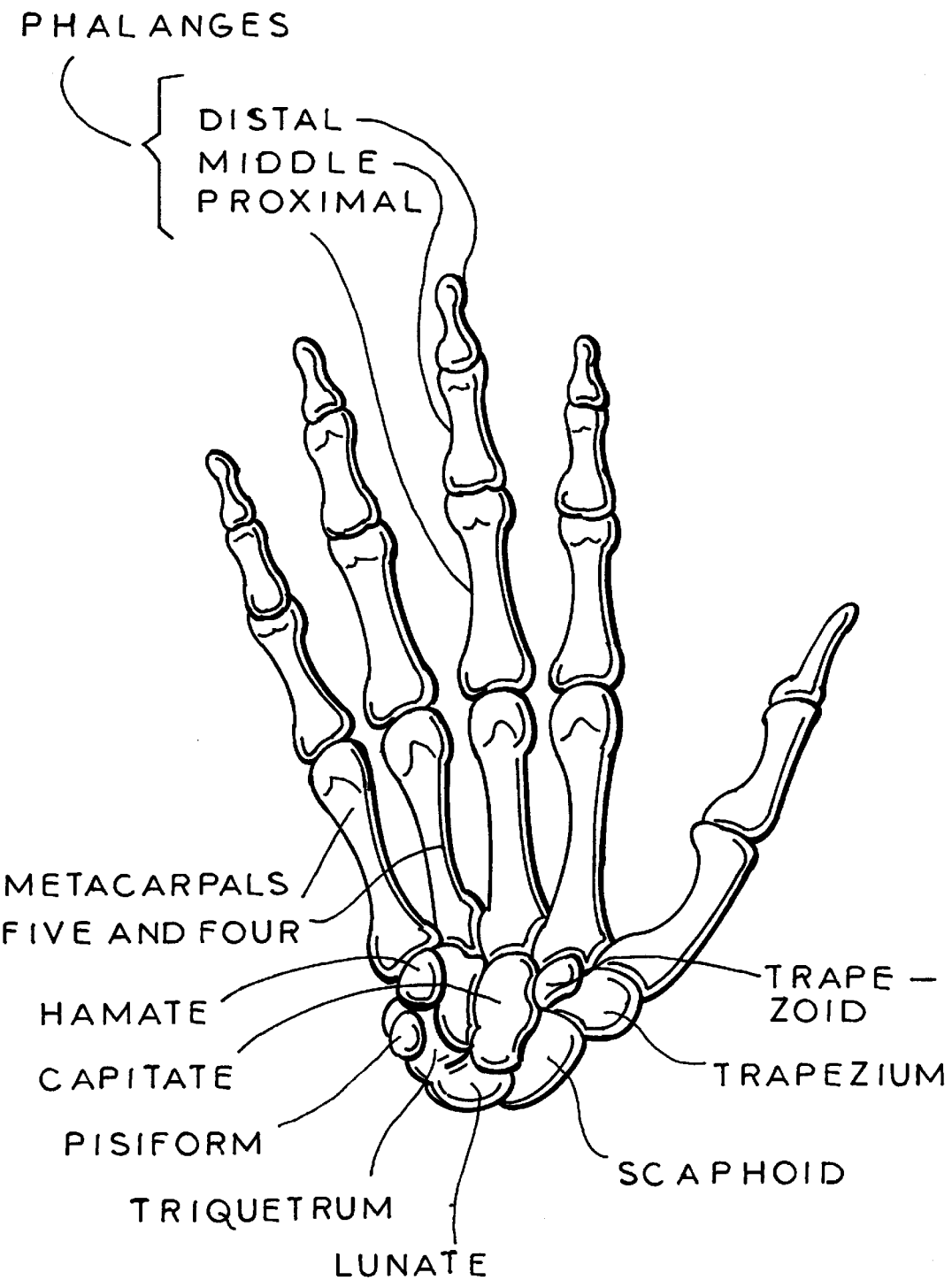
FIG. 10 is a skeletal view of the palmar aspect of the right hand.

Referring to, During treatment, the bladder 22 is inflated with the source of pressurized fluid 24 to apply force to the dorsal aspect of the hand 12, which force is balanced by separate forces applied in an opposite direction by the thenar and hypothenar portions 14, 18 to their respective areas of the palmar aspect of the hand. Referring to FIGS. 8 and 9, this arrangement of forces causes the distance between certain carpal bones of the hands to increase, namely the pisiformis and hamulus of hamate bones, thereby stretching the carpal ligament and the flexor retinaculum. The pressure is maintained at a preferably constant level for a period of time to induce permanent or semipermanent elongation of the carpal ligament and the flexor retinaculum, thereby increasing the diameter of the carpal tunnel and decreasing the cause and symptoms of carpal tunnel syndrome.

Referring again to FIGS. 1–3, the appliance 10 preferably maintains the hand 12 in the neutral position during treatment. In addition, the thumb 16 is maintained in radial abduction. This position minimizes the natural internal pressure in the carpal tunnel which aids in treatment. When pressure is applied to the bladder 22, the upward force on the dorsal aspect of the hand 12, balanced in part by the opposing force on the hypothenar area of the palmar aspect of the hand 12, will naturally cause the thumb 16 to move into a mild or slight retroposition (i.e., slightly bent downward with respect to the palm).

The thenar and hypothenar portions 14, 18, and the bladder 22, each have relatively large contact areas of preferably at least about 6.25 cm$^2$, 7.25 cm$^2$, and 13.5 cm$^2$, respectively, such that the forces applied to the associated areas of the hand 12 are widely distributed. The wide distribution of forces applied to the hand increases the comfort of the appliance during treatment, and minimizes any detrimental effects of the pressure to the epidermis, and increases the length of time for which the appliance can be used.

Referring to FIGS. 1–3 and FIG. 10, the hypothenar portion 18 of the appliance 10 extends from adjacent the distal ends of the metacarpal bones of the fourth and fifth digits on the palmar aspect of the hand to a position preferably about three inches proximal to (i.e., above, or closer to the chest than) the pisiform bone. Thus the appliance 10 covers the hypothenar muscles and a portion of the ulnar aspect of the distal forearm. The dorsal portion 20 of the appliance 10 extends from adjacent the distal ends of the metacarpal bones of digits one through four, inclusive, to a position (preferably three inches) proximal to the wrist joint. A projection extends from the radial aspect of the dorsal portion 20.

As mentioned above, the hypothenar portion 18 also preferably includes a proximal end portion 62. This proximal end portion 62 preferably extends beyond the carpal bones at the proximal end 60 of the hand 12, thereby essentially immobilizing the hand 12 during treatment.

The dorsal portion 20 goes around the posterior aspect of the hand 12 covering from adjacent the distal ends of the metacarpal bones of digits one to four, inclusive, to three inches proximal to the wrist joint.

The bladder 22 preferably extends longitudinally about 3 inches, from adjacent the distal ends of the metacarpal bones of at least the third through fourth fingers to adjacent or over the carpal bones, and transversely, about 2 inches.

The dorsal portion 20 of the appliance preferably has a distal end portion 68 which extends longitudinally, beyond the bladder 22, to maintain the hand 12 in the neutral position during treatment.

Carpal tunnel treatment protocols using the appliance 10 consist of applying either constant or varying pressure to the dorsal aspect of the hand for predetermined periods of time at preferably regular intervals. The design of the appliance 10 is such that, once given proper instruction, treatment can be administered by the patient without the aid of a physician or other assistant. The pressurized source of fluid 24 and the pressure gauge 32 provide that the forces applied to the hand 12 can be accurately and easily monitored and duplicated. In addition, the forces can be adjusted while the appliance 10 is fully mounted on the hand 12. As mentioned above, the appliance 10 can include a means to limit the maximum amount of pressure in the bladder 22, such as a pressure release valve, to prevent accidental overstressing of the carpal ligament and flexor retinaculum.

Referring to FIGS. 4–7, an alternate preferred embodiment of the appliance 110 includes a detachable thenar portion 114 which is designed to aid in the mounting of the appliance for extreme cases of carpal tunnel syndrome. The detachable thenar portion 114 extends outwardly over the palmar aspect of the hand 12 and is secured to both a dorsal portion 120 and a thumb support extension 121 of the dorsal portion by a securing means 70 such as an elastic strap 72 and releasable fastening means, such as Velcro® hook-and-loop fasteners, snaps, or the like. The securing means 70 is preferably connected to the dorsal portion 120, the thumb support extension 121, the detachable thenar portion 114 and the hypothenar portion 118 by fasteners 74, such as Velcro® hook-and-loop fasteners attached to the areas of contact.

As with the first embodiment of the appliance 10, the second embodiment of the appliance 110 includes a bladder 122, a source of pressurized fluid 124, and a pressure gauge 132 for applying pressure to the dorsal aspect of the hand 12.

Figure 4:
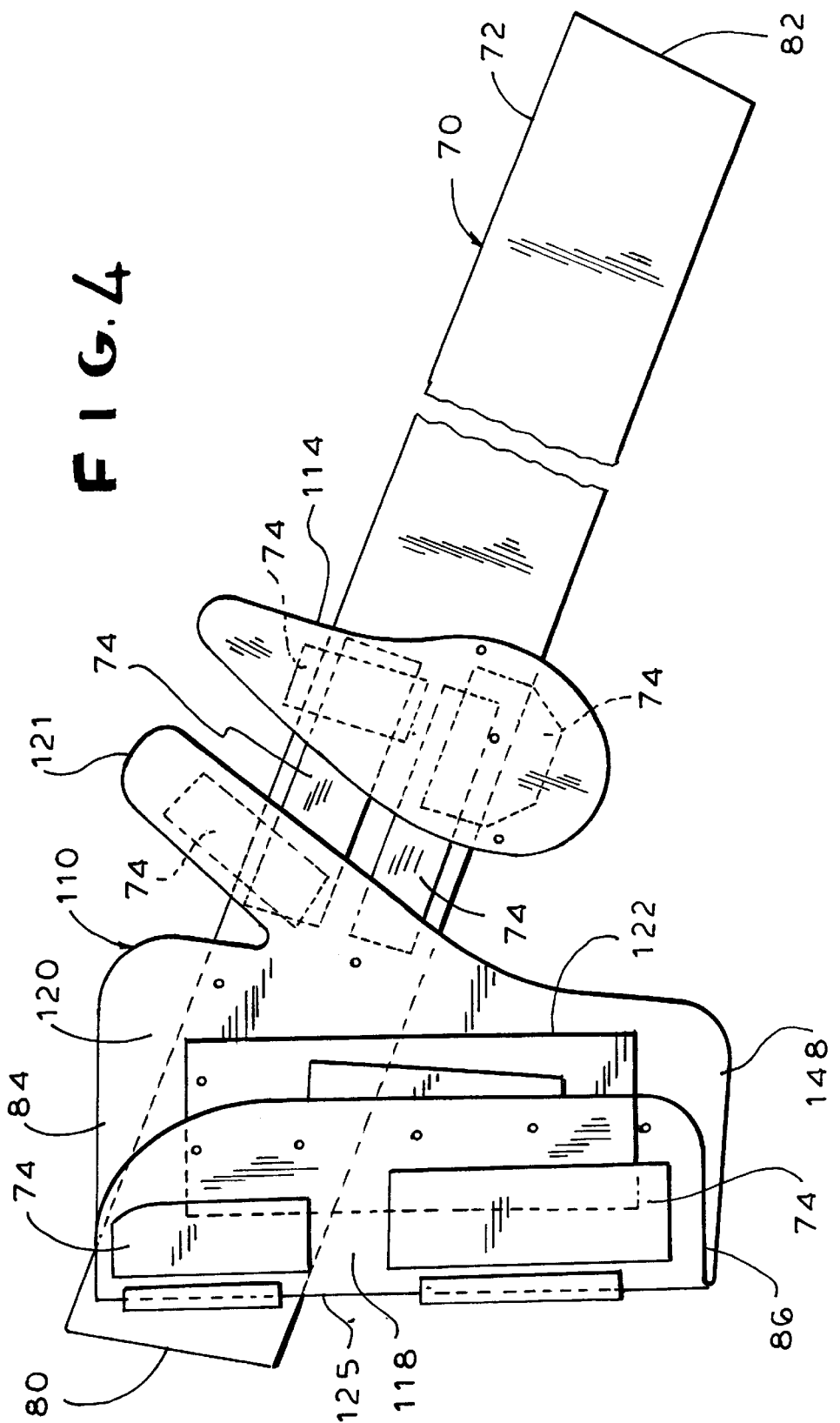
FIG. 4 is a top plan view of a second embodiment of the therapeutic appliance.

In donning the appliance 110, the medial aspect of the hand is inserted between the hypothenar position 118 and the dorsal portion 120, with the thumb 16 resting on the thumb support extension 121 of the dorsal portion 120, and the detachable thenar position 114 and the securing means 70 in a detached position, as shown in FIG. 4.

Figure 5:
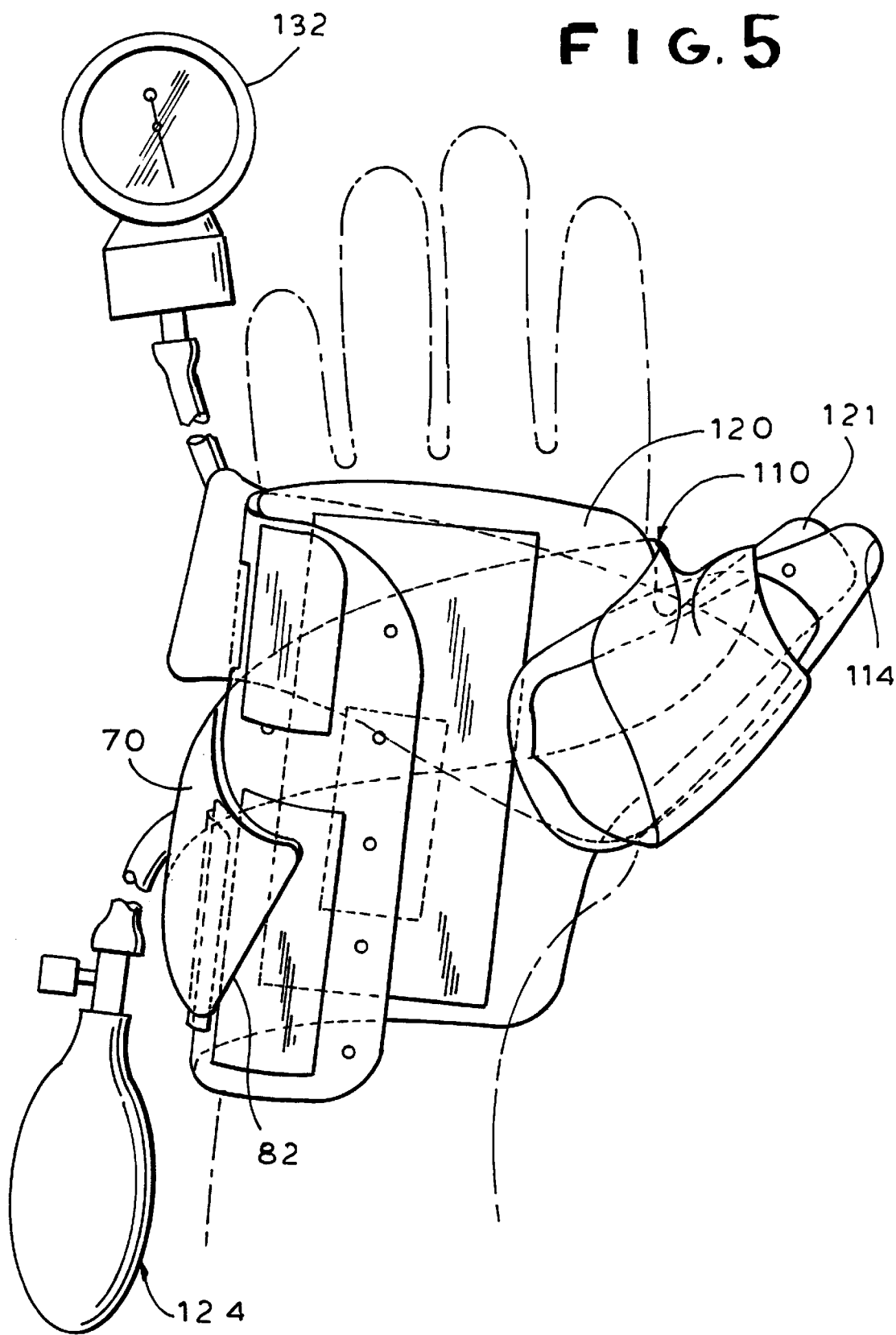
FIG. 5 is a top plan view of the appliance of FIG. 4, mounted on a hand.
Figure 6:
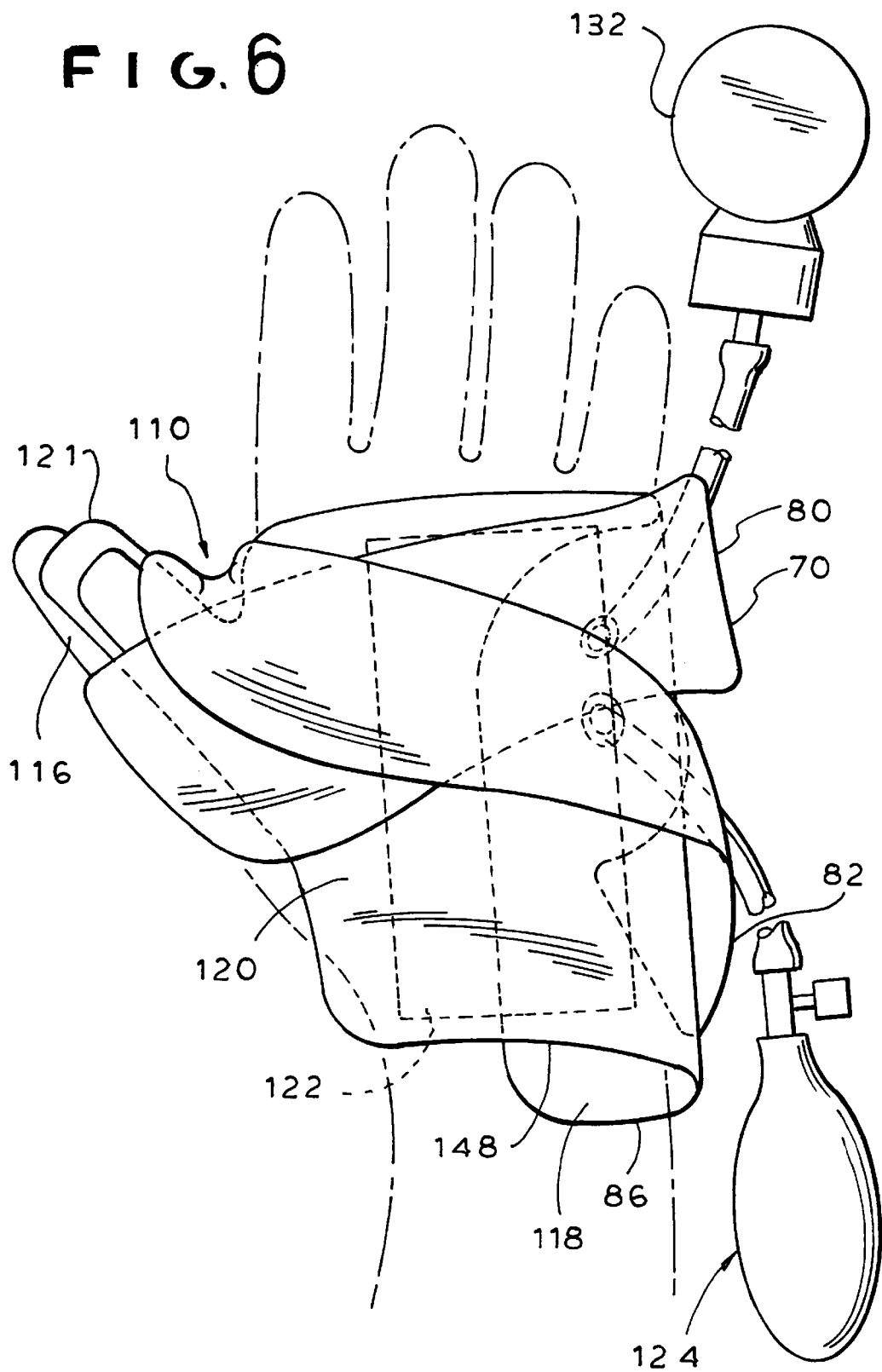
FIG. 6 is a bottom plan view of the appliance of FIG. 5.
Figure 7:
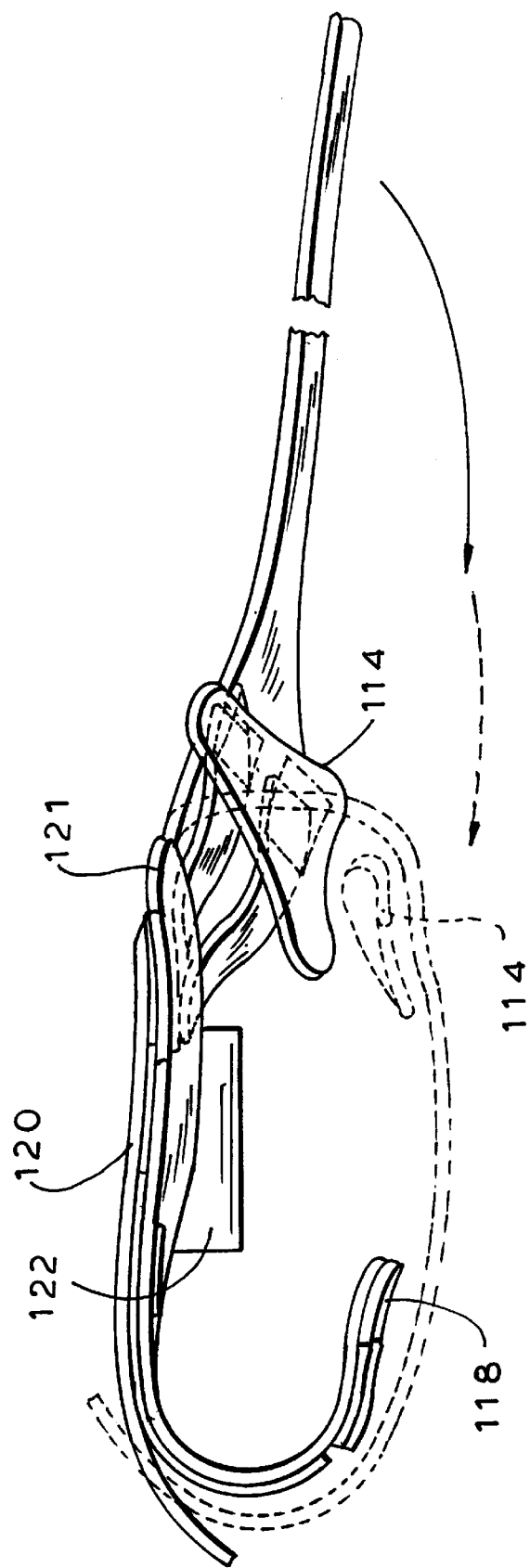
FIG. 7 is a distal end elevational view of the appliance of FIG. 4, illustrating the method of donning the appliance.

As depicted in FIG. 5, the securing means 70 has one end 80 attached to the appliance 110, preferably adjacent a medial side 125 of a distal end portion 84 of the hypothenar portion 118. The securing means 70 is wrapped around the thumb 16, thereby aligning the detachable thenar portion 114 with the thenar area of the palmar aspect of the hand 12 and confining the thumb 16 between the thenar portion 14 and the thumb-support extension 121 of the dorsal portion 120. This secures the thumb 16 in radial abduction.

The securing means 70 is then extended underneath the dorsal portion 120 and a second end 82 is attached to the appliance 110, preferably adjacent the medial side 125 near the proximal end portions 148, 86, respectively of either the dorsal portion 120 or the hypothenar portion 118.

It can be appreciated that, once the securing means is properly attached, the position of the detachable thenar portion 114 is substantially fixed with respect to the dorsal portion 120 and the other parts of the appliance 110. Therefore, once pressure is applied to the bladder 122, the appliance 110 will function to stretch the carpal ligament and flexor retinaculum as discussed in conjunction with the first embodiment of the appliance.

The appliance and method of the invention provide a novel, convenient, and effective means to treat carpal tunnel syndrome. The appliance of the invention of relatively inexpensive, comfortable, and easy to operate. Furthermore, the force applied to the hand can be precisely set, monitored, and adjusted, thereby increasing the effectiveness of the appliance and method.

It should be understood, of course, that the specific forms of the invention herein illustrated and described are intended to be representative only, as certain changes may be made therein without departing from the clear teachings of the disclosure. Accordingly, reference should be made to the following appended claims in determining the full scope of the invention.

I claim:

1. An appliance for treating carpal tunnel syndrome, comprising:

(a) a splint for applying pressure substantially only to a dorsal aspect of the hand and to thenar and hypothenar areas of a palmar aspect of the hand, said splint including rigid dorsal, thenar and hypothenar portions;

(b) said dorsal portion of said splint having first and second opposed sides, said dorsal portion being sized and configured to support a dorsal aspect of the hand;

(c) said thenar portion of said splint being connected to said first side of said dorsal portion, being spaced from said dorsal portion and being located between said first and second sides of said dorsal portion of said splint;

(d) said hypothenar portion of said splint being connected to said second side of said dorsal portion, being spaced from said dorsal portion and being located between said first and second sides of said dorsal portion of said splint;

(e) said splint being sized and shaped to receive the hand with the dorsal, thenar and hypothenar portions of said splint substantially aligned with and covering the respective dorsal aspect, and thenar and hypothenar areas of the palmar aspect of the hand;

(f) an inflatable bladder attached only to said dorsal portion of said splint and located to contact, when the hand is inserted into the splint, the dorsal aspect of the hand between said thenar and hypothenar areas of the palmar aspect of the hand; and (g) a controllable source of pressurized fluid connected to said bladder;

(h) said bladder being located to apply a controllable, first distributed force only to the dorsal aspect of the hand when in use, and said first force being balanced only by second distributed forces applied to the thenar and hypothenar areas of the palmar aspect of the hand by said thenar and hypothenar portions of the splint, respectively; said first and second forces causing the carpal bones to separate to stretch the carpal ligament and flexor retinaculum, to effectuate enlargement of the diameter of the carpal tunnel and concomitant reduction of pressure on a median nerve; said source of pressurized fluid being controllable to adjust the pressure applied to the hand while the hand is in said splint;

(i) said splint being formed of a unitary piece of material that includes lateral and medial joining portions which connect said thenar and hypothenar portions of said splint, respectively, to said respective first and second sides of said dorsal portion of said splint; and (j) said lateral joining portion of said splint having a hole to accommodate the passage of the thumb therethrough.

2. An appliance according to claim 1, wherein said splint is sized and shaped to follow the contours of the dorsal aspect and the thenar and hypothenar areas of the palmar aspect of the hand such that the hand is closely received within said splint during treatment.

3. A method for treating carpal tunnel syndrome, comprising:

(a) providing a splint for applying pressure substantially only to a dorsal aspect of the hand and to thenar and hypothenar areas of a palmar aspect of the hand, said splint including rigid dorsal, thenar and hypothenar portions;

(i) said dorsal portion of said splint having first and second opposed sides, said dorsal portion being sized and shaped to support a dorsal aspect of the hand;

(ii) said thenar portion of said splint being connected to said first side of said dorsal portion, being spaced from said dorsal portion, and being located between said first and second sides of said dorsal portion of said splint;

(iii) said hypothenar portion of said splint being connected to said second side of said dorsal portion, being spaced from said dorsal portion, and being located between said first and second sides of said dorsal portion of said splint; and (iv) said splint being sized and shaped to receive the hand with the dorsal, thenar and hypothenar portions of said splint substantially aligned with and covering the respective dorsal aspect, and thenar and hypothenar areas of the palmar aspect of the hand;

(b) providing an inflatable bladder attached only to said dorsal portion of said splint and located to contact, when the hand is inserted into the splint, the dorsal aspect of the hand between said thenar and hypothenar areas of the palmar aspect of the hand;

(c) providing a controllable source of pressurized fluid connected to said bladder;

(d) inserting the hand into said splint;

(e) inflating said bladder with said controllable source of pressurized fluid; and (f) maintaining a substantially constant pressure level in said bladder for a predetermined treatment period;

(g) said bladder applying a controllable, first distributed force only to the dorsal aspect of the hand;

(h) said first force being balanced only by second distributed forces applied to the thenar and hypothenar areas of the palmar aspect of the hand by said thenar and hypothenar portions of the splint, respectively;

(i) said first and second forces causing the carpal bones to separate to stretch the carpal ligament and flexor retinaculum, to effectuate enlargement of the diameter of the carpal tunnel and concomitant reduction of pressure on a median nerve; and (j) said source of pressurized fluid being controllable to adjust the pressure applied to the hand while the hand is in said splint.

4. The method according to claim 3, wherein said bladder is attached to an interior surface of said dorsal portion of said splint between said dorsal portion of said splint and said thenar and hypothenar portions of said splint.

5. The method according to claim 4, wherein:

(a) said splint is formed of a unitary piece of material that includes lateral and medial joining portions which connect said thenar and hypothenar portions of said splint, respectively, to said respective first and second sides of said dorsal portion of said splint; and (b) said lateral joining portion of said splint has a hole to accommodate the passage of the thumb therethrough.

6. The method according to claim 5, wherein said splint is sized and shaped to follow the contours of the dorsal aspect and the thenar and hypothenar areas of the palmar aspect of the hand such that the hand is closely received within said splint during treatment.

7. The method according to claim 6, wherein said thenar portion of said splint has an inserting position wherein the hand of the user can be inserted into said appliance without substantial manipulation of the inserted hand or the digits thereof, and said thenar portion of said splint has a treatment position wherein said thenar portion is substantially fixed with respect said dorsal portion of said splint and is spaced from said dorsal portion in a location between said first and second sides of said dorsal portion of said splint.

8. The method according to claim 3, further comprising a pressure gauge connected to said bladder.

9. The method according to claim 3, wherein said controllable source of pressurized fluid comprises a hand pump operable by the user of said appliance.

10. The method according to claim 3, wherein said dorsal portion of said splint or said hypothenar portion of said splint extends over a portion of the distal forearm of user when the hand is inserted into said splint such that the motion of the hand, when inserted into said splint, is limited in extension or flexion to assist in maintaining the hand in a substantially neutral position during treatment.

11. The method according to claim 3, wherein said dorsal portion of said splint and said hypothenar portion of said splint each extend over a portion of the distal forearm of user when the hand is inserted into said splint such that the motion of the hand, when inserted into said splint, is limited both in extension and flexion to maintain the hand in a substantially neutral position during treatment.

* * * * *